(12) United States Patent
Haneef et al.

(10) Patent No.: US 11,701,461 B2
(45) Date of Patent: Jul. 18, 2023

(54) DUAL LUMEN EXTRACORPOREAL MEMBRANE OXYGENATION CATHETER WITH SINGLE ENTRY PORT BYPASSING THE RIGHT HEART AND LUNGS

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Ali Ahmed Haneef, Riyadh (SA); Abdelhamid Saoudi, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 862 days.

(21) Appl. No.: 16/711,613

(22) Filed: Dec. 12, 2019

(65) Prior Publication Data
US 2021/0178047 A1 Jun. 17, 2021

(51) Int. Cl.
*A61M 1/36* (2006.01)
*A61M 1/16* (2006.01)
(Continued)

(52) U.S. Cl.
CPC ........ *A61M 1/3659* (2014.02); *A61M 1/1698* (2013.01); *A61M 1/267* (2014.02);
(Continued)

(58) Field of Classification Search
CPC .. A61M 1/1698; A61M 1/267; A61M 1/3659; A61M 1/3666; A61M 1/3667;
(Continued)

(56) References Cited

U.S. PATENT DOCUMENTS

2002/0128586 A1* 9/2002 Barbut ................ A61M 1/3659
604/113
2016/0008531 A1* 1/2016 Wang .................... A61M 60/38
600/16
(Continued)

FOREIGN PATENT DOCUMENTS

WO 2017/186831 A1 11/2017

OTHER PUBLICATIONS

Jayaraman, et al. ; Cannulation Strategies in Adult Veno-arterial and Veno-venous Extracorporeal Membrane Oxygenation: Techniques, Limitations, and Special Considerations; Annals of Cardiac Anaesthesia, vol. 20, Special Issue 1 ; Jan. 2017 ; 8 Pages.

(Continued)

*Primary Examiner* — Benjamin J Klein
(74) *Attorney, Agent, or Firm* — Oblon, McClelland, Maier & Neustadt, L.L.P.

(57) ABSTRACT

The invention pertains to a medical device: an ECMO (extracorporeal membrane oxygenation) catheter which can be used during right heart and lung failure. It pertains to a dual lumen catheter with a single port of entry which when in place bypasses the right heart and lungs while completing the veno-arterial circuit.

16 Claims, 8 Drawing Sheets

(51) Int. Cl.
*A61M 25/00* (2006.01)
*A61M 1/26* (2006.01)

(52) U.S. Cl.
CPC ........ *A61M 1/3666* (2013.01); *A61M 1/3667* (2014.02); *A61M 25/0026* (2013.01); *A61M 25/0041* (2013.01); *A61M 25/0067* (2013.01); *A61M 25/0068* (2013.01); *A61M 25/0074* (2013.01); *A61M 2025/0034* (2013.01); *A61M 2025/0037* (2013.01); *A61M 2210/125* (2013.01)

(58) Field of Classification Search
CPC .......... A61M 25/0026; A61M 25/0041; A61M 25/0067; A61M 25/0068; A61M 25/0074; A61M 2025/0034; A61M 2025/0037; A61M 2210/125
See application file for complete search history.

(56) References Cited

U.S. PATENT DOCUMENTS

| | | | |
|---|---|---|---|
| 2016/0022896 A1* | 1/2016 | Burkhoff | A61M 1/3621 600/17 |
| 2016/0114124 A1* | 4/2016 | Tal | A61M 1/3661 604/43 |
| 2018/0085514 A1 | 3/2018 | Kelly et al. | |
| 2018/0104402 A1 | 4/2018 | Ahmad et al. | |
| 2021/0220542 A1* | 7/2021 | Heilmann | A61M 1/1698 |
| 2022/0323663 A1* | 10/2022 | Heilmann | A61M 1/3661 |

OTHER PUBLICATIONS

Rao, et al.; Venoarterial Extracorporeal Membrane Oxygenation for Cardiogenic Shock and Cardiac Arrest; Circulation: Heart Failure; Sep. 2018; 17 Pages.

* cited by examiner

DUAL LUMEN EXTRACORPOREAL MEMBRANE OXYGENATION CATHETER WITH SINGLE ENTRY PORT BYPASSING THE RIGHT HEART AND LUNGS

BACKGROUND OF THE INVENTION

Field of the Invention

The invention falls within the field of medicine, specifically endovascular surgery. It pertains to a medical device: an ECMO (extracorporeal membrane oxygenation) catheter which can be used during a right heart and lung failure. It pertains to a dual lumen catheter with a single port of entry which when in place bypasses the right heart and lungs while completing the veno-arterial circuit.

Description of Related Art

Figure 1:
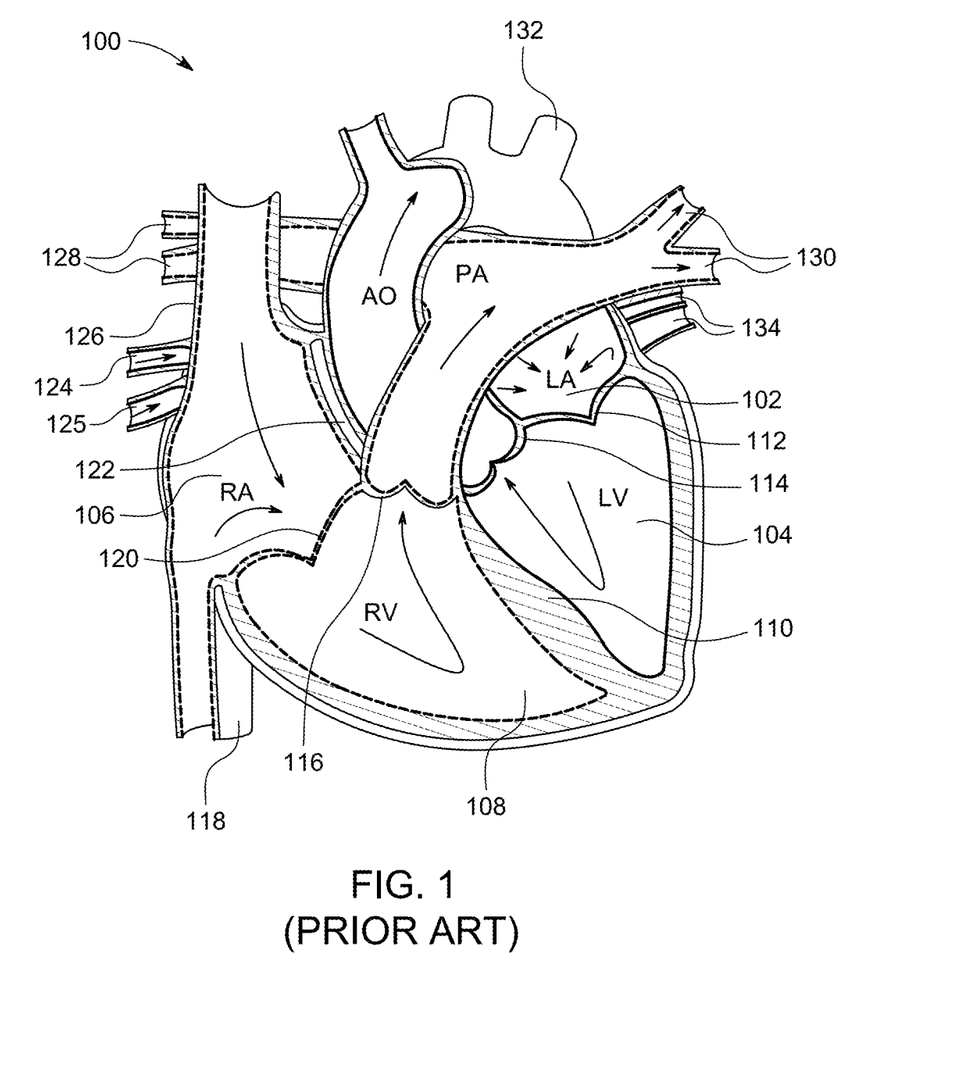

In the normal heart oxygen-depleted (venous) blood enters the right atrium (RA) via the superior and inferior vena cava. The venous blood then passes through the right ventricle (RV) and is pumped via the pulmonary artery (PA) to the lungs where it adsorbs oxygen and becomes oxygenated arterial blood. Oxygenated arterial blood is then returned vial the pulmonary veins to the left atrium (LA) and is passed to the left ventricle (LV) where it is pumped through the aorta (A) to the body; FIG. 1.

When the lungs are damaged or incapable of sufficiently oxygenating venous blood, an oxygenation device located outside the body can be used to oxygenate the blood. Extracorporeal membrane oxygenation, or ECMO, is an advanced life support technique used for patients with life-threatening heart and/or lung problems. ECMO provides long-term breathing and heart support and is typically used only when all standard treatments for those problems have already been tried. A highly specialized treatment, ECMO can support patients for days to weeks while doctors treat their underlying illness. The oxygenation of the blood and removal of $CO_2$ is extracorporeal and occurs outside of the body. The membrane is a type of artificial lung that oxygenates blood which provides oxygenation to blood circulated outside of the body and then back into the body.

ECMO is usually performed using a heart-lung bypass machine similar to the one used during open heart surgery. The ECMO machine, often referred to as a "circuit," is quite large and contains sterile plastic tubing that moves blood from a patient's body to the "ECMO lung" and then back into the patient. The ECMO lung adds oxygen to the blood and removes carbon dioxide, as a healthy lung would.

Figure 2A:
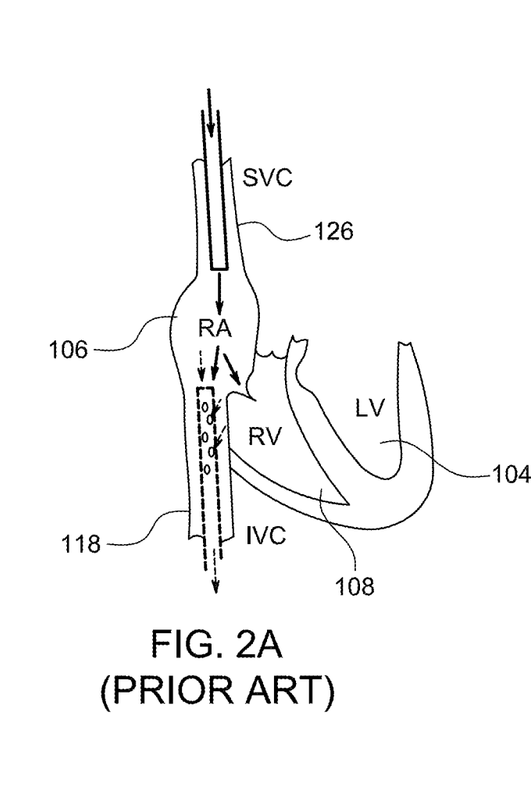
Figure 2B:
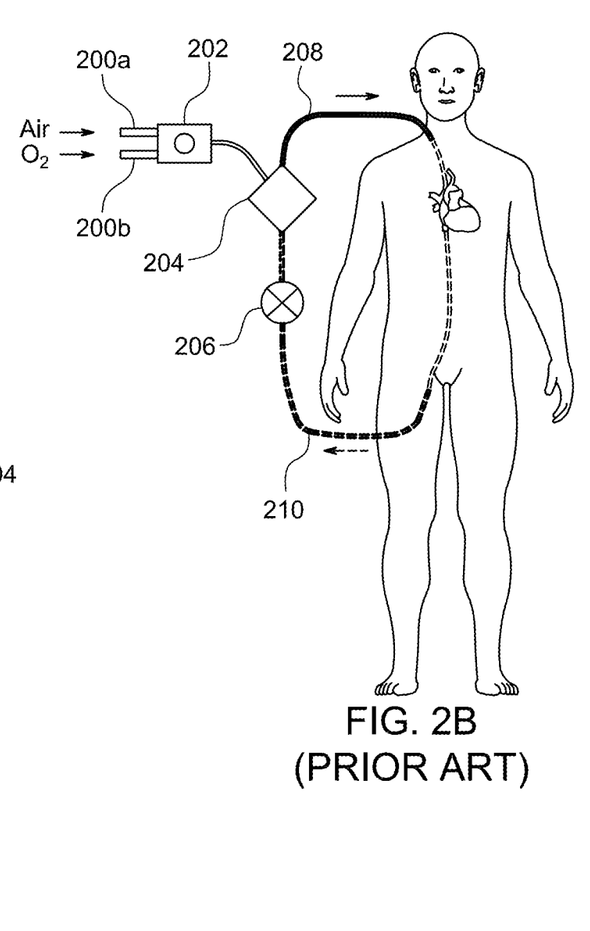
FIG. 2B provides a comparison of femoral and central cannulization for conventional two catheter, two insertion point V-A ECMO. Reference characters depict air 200a and $O_2$ 200b lines which connect to blender 202. Blended air/oxygen mixture is fed to oxygenator 204 and oxygenated blood is pumped into patient via catheter 208 and out of patient via catheter 210 by pump 206.
Figure 2C:
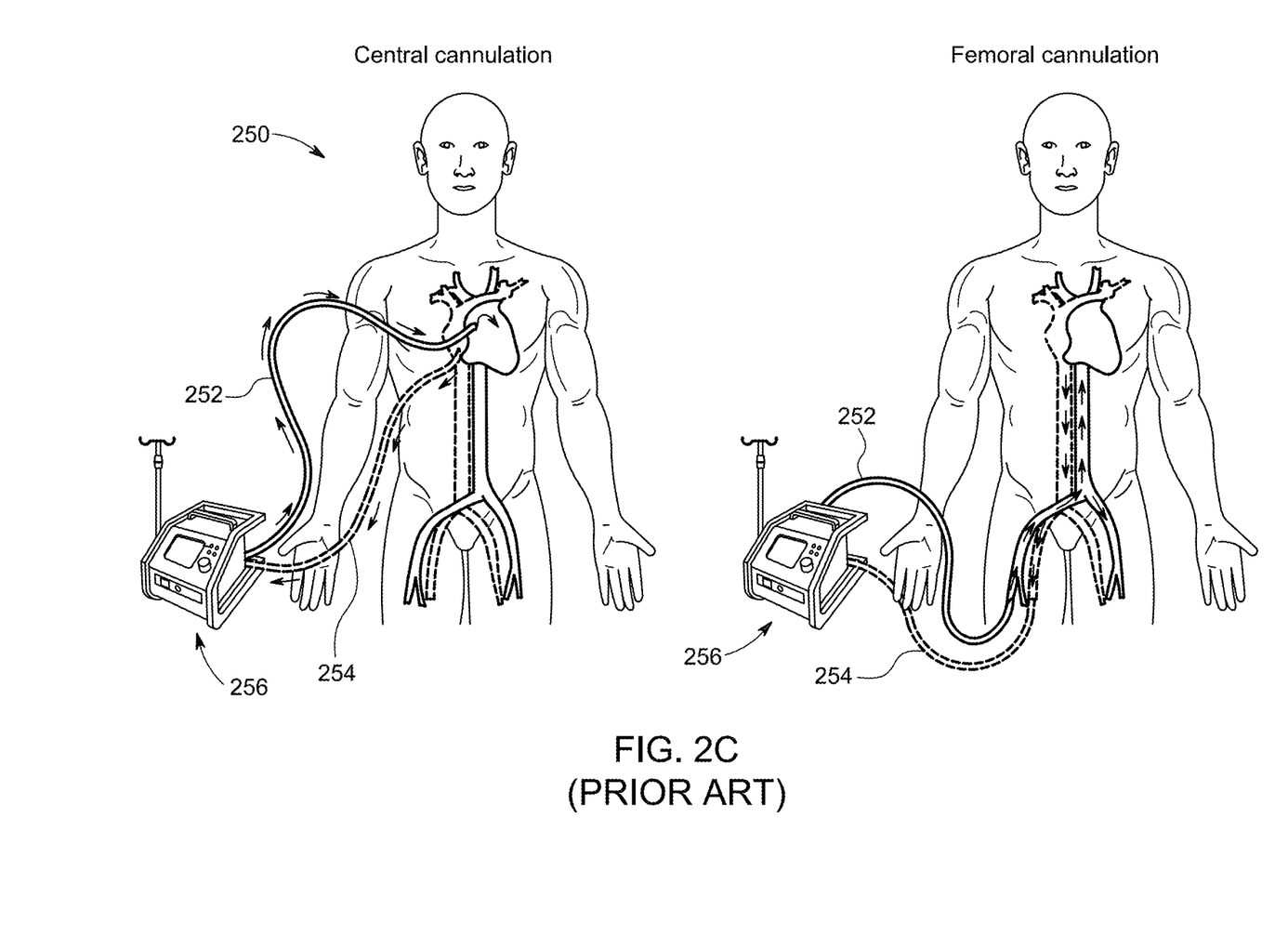
FIG. 2C provides a comparison 250 of V-A central and femoral cannulation. Reference characters refer depict oxygenator 256 and two point catheter entries via catheters 252 and 254.
Figure 2D:
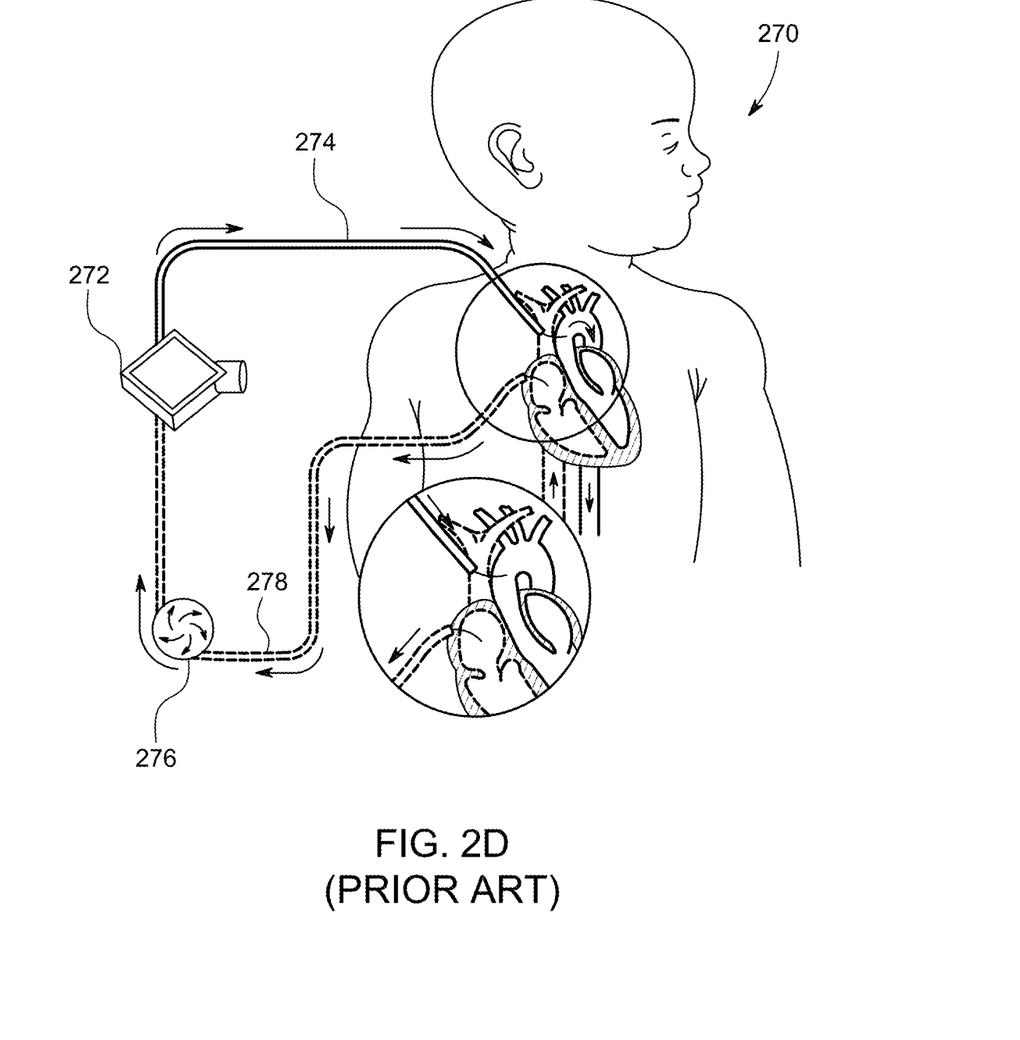
FIG. 2D depicts a dual catheter ECLS 270 comprising an oxygenator 272, centrifugal pump 276 and two point catheter entries into the aorta 274 and right atrium 278.

There are two types of ECMO. Venovenous (V-V) ECMO is used when the heart is functioning well and only the lungs need to rest and heal; FIG. 2A, and venoarterial (V-A) ECMO is used when the heart as well as the lungs need to rest and heal; FIGS. 2C and 2D.

Gregory, et al., Crit. Care Med. 43(12) describes a (V-V) ECMO comprising bicaval dual-lumen catheters for patients undergoing veno-venous extracorporeal membrane oxygenation and Javidfar, J. et al., ASAIO J. 2014 January-February; 60(1): 129-33, describes a bicaval dual lumen extracorporeal membrane oxygenation catheter. ECMO has been considered for right heart failure in group 1 pulmonary arterial hypertension; Rosenzweig E. B., et al., Eur J Cardiothorac Surg. 2017 Oct. 16. doi: 10.1093/ejcts/ezx349 and for right ventricular failure after left ventricular assist device implantation, Riebandt, et al., Ann Thorac Surg. 2011 June; 91 (6): 1763-8; discussion 1769. doi: 10.1016/j.athoracsur.2011.03.002. WO2017186831 A1 describes a catheter device that requires two entry points.

Javidfar, J., et al. report use of a single-site, dual-lumen cannula for venovenous (V-V) ECMO as an alternative to a 2-catheter approach. However, presently available V-A catheters require two point of entry to complete the cardiopulmonary circuit as shown by FIGS. 2B and 2C.

A significant drawback of both V-A ECMO and V-V ECMO catheters is the requirement for ligation of two primary veins and/or arteries. It is generally accepted that ligation poses the threat of future neurologic complications. Attempts to solve this problem have led to procedures involving a single ligation and cannulation, which use a tidal flow method (TF). With tidal flow, the action of withdrawal and perfusion are mutually exclusive with respect to time through the same passage in a single cannula. While tidal flow ECMO reduces the number of ligations from two to one it does not permit continuous and simultaneous withdrawal and perfusion of blood. Moreover, it results in recirculation of a mixture of venous blood with oxygenated blood because both blood withdrawal and return occur at the same site.

During right heart failure and/or lung failure the aim of ECMO is to rest the right heart and/or the lungs during the cardiopulmonary bypass (CPB). However, this is not sufficiently achieved by the veno-venous (V-V) ECMO and can be only attained by the veno-arterial (V-A) ECMO which conventionally requires two ports of entries for the arterial catheter and venous catheter. Conventional V-A catheters require a two port access to complete the CPM circuit to oxygenate venous blood and provide oxygenated (arterial) blood back to the patient, see FIGS. 2C and 2D.

With these limitations and drawbacks to endovascular ECMO catheters in mind, the inventors sought to design an ECMO catheter that permits the reduction of the number of ligations required to provide extracorporeal life support system (ECLS) to one ligation without the limitations of the tidal flow ECMO.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

The invention involves a catheter designed for a single venous port access to the heart and to the use of this catheter for treating right heart failure, lung failure, or failure of both the right heart and lungs. This device bypasses the right heart and can permit lung bypass when there is lung damage or morbidity, for example, after a coronavirus infection or other viral, fungal or bacterial infection. The catheter permits the heart and/or lungs to rest and recover all or part of their normal functions.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIG. 1. Schematic of normal heart showing direction of blood flow through the four heart chambers. Reference characters show: right pulmonary arteries 128; superior vena cava (SVC) 126; right pulmonary veins 124, 125; atrial septum 122; right atrium 106; tricuspid valve 120; inferior vena cava (IVC) 118; pulmonary valve 116; right ventricle 108; ventricular septum 110; left ventricle 104; aortic valve 114; mitral valve 112; left atrium 102; pulmonary veins 134; left pulmonary arteries 130; aorta 332.

FIG. 2A depicts femoral cannulization for V-V ECMO. Oxygenated blood is pumped into the superior vena cava 126 and oxygen-depleted blood pumped out via a cannula in the inferior vena cava (IVC) 118. Reference characters also depict right atrium 106; IVC 118; right ventricle 108; and left ventricle 104.

DETAILED DESCRIPTION OF THE INVENTION

Embodiments of the invention include the following.

One embodiment of the invention is directed to a dual lumen single entry point catheter comprising (i) a proximal segment comprising a section of two unjoined cannulas one suitable for transporting (injecting) arterial blood (lumen a) and the other suitable for transporting (aspirating) venous blood (lumen b), (ii) a central segment wherein cannula (a) and cannula (b) are longitudinally joined (e.g. as a dual lumen segment with lumen (a) and lumen (b) coaxially aligned), and (iii) a distal segment wherein cannula (a) and cannula (b) are not joined (e.g., branch from central dual lumen portion (ii)); wherein lumens (a) and (b) in the proximal segment (i) are configured to operably connect to an exterior oxygenation device with cannula (a) connected so as to receive oxygenated blood from the membrane and cannula (b) connected so as to deliver venous blood to the oxygenation device, wherein in the central segment (ii) the joined lumens are configured to make a single point insertion into the right atrium of the heart via the vena cava, and wherein in distal segment (iii) cannula (a) is configured so as to penetrate the wall between the right and left atrium and enter the left atrium so as to be able to deliver arterial blood into the left atrium, and wherein in distal segment (iii) cannula (b) is configured to fit within the right atrium and enter the vena cava so as to receive venous blood and deliver it to the exterior oxygenation membrane. Nonlimiting embodiments of this catheter are described by FIGS. 3A, 3B and 3C. In some embodiments, section (i) of the dual lumen cannula may be attached to section (ii) where cannulas (a) and (b) are attached by a y-shaped or branched fitting as shown in FIG. 4A or 4B The distal segment (iii) is distal to the single entry point in the vena cava, the central segment (ii) is located within the right atrium and vena cava, and the proximal segment (i) is positioned prior to the single entry point into the vena cava and outside of the right atrium. The catheters are narrow at the insertion to facilitate penetration and insertion into the lumen of the vessels.

In some embodiments the dual lumen single entry port catheter is configured so as to permit the single point insertion to occur via the superior vena cava (SVC) and wherein the lumen (b) is configured to receive venous blood from the inferior vena cava.

In other embodiments the dual lumen single entry port catheter is configured so as to permit the single point insertion to occur via the inferior vena cava (SVC) and wherein the cannula (b) is configured to receive venous blood from the superior vena cava.

In some embodiments, the length of cannula (a) in the distal segment (iii), wherein cannula (a) and cannula (b) are not attached, ranges from about 2, 2.5, 3, 3.5, to 4 cm and the length of cannula (b) ranges from about 4, 5, 6, 7, 8, 9 to 10 cm. Generally, cannula (b) which extends downward into the inferior vena cava, or in another embodiment, upward into the superior vena cava is longer than cannula (a) which inserts into the left atrium. The exact lengths and diameters of cannula (a) and cannula (b) may be selected by one skilled in the medical arts based on the shape and size of the heart and related cardiovascular structures.

The cannulas do not tightly fit into the lumen of the vena cava to avoid obstruction of the drainage of blood to the heart. The extension passes through the atrial septum into the Left atrium. Sizes of the cannulas vary based upon the body surface area of a patient and can range from: 13 Fr. (4.3 mm) up to 31 Fr (10.3 mm) in diameter. The insertable length ranges from 10, 11, 15, 20, 25, 30 to 31 cm and the left atrial extension ranges from about 2-4 cm in length.

Catheters are typically kink-resistant material and can be wire-reinforced and radiopaque. They may contain a deflectable inner membrane and distal and proximal drainage ports.

They may be heparin coated and contain separate drainage in infusion ports. Catheters may have color markings on the ports of drainage and infusion to indicate the positions of the infusion and drainage holes. They may have radio-opaque markers at the extension of the limb that goes into the left atrium via the atrial septum. Cannulas are typically secured to the skin or other tissues with sutures to avoid displacement.

While arterial blood is generally at higher pressure than venous blood, the extension of the left atrium passes through the atrial septum which is pierced under imaging (Echo guided) This hole is small and it will fit and does not allow for significant flow of blood from left atrium to right atrium.

Cannula (a) and cannula (b) have a gauge suitable for performing ECMO is a particular patient and can range in gauge size as well as length depending on the weight or size of the patient's heart and vasculature. In some embodiments, these lumens range in gauge from at least 10, 12, 14, 16, 18, 20, 22, 24, 26, 28, 30, 32, 34, 36, 38, 40 and >40 French (Fr).

A patient treated using the catheter as disclosed herein may be a neonate, or no more than 1, 2, 3, 4, 5, 6, 7, 8, 9, 10, 11, 12, 13, 14, 15, 16, 17, 18, 19, 20, 21, 25, 30, 35, 40, 45, 50, 55, 60, 65, 70, 75, 80, 85, 90, 95, 100 or >100 years old. The catheter disclosed herein and its component parts may be sized in length, gauge and blood flow rate or capacity so as to provide ECMO to such patients.

Another embodiment of the invention is directed to an extracorporeal membrane oxygenation (ECMO) system or extracorporeal life support (ECLS) system comprising the dual lumen single entry point catheter as disclosed herein, a device that removes $CO_2$ and oxygenates blood, a pump, and tubing, such as silicone tubing, that operably connects the catheter and device so as to permit the passage of blood.

A further embodiment of the invention is directed to a method for treating a patient having right heart failure, lung failure, or both, comprising positioning the single entry point, dual lumen catheter as disclosed herein into the heart of the patient; wherein the proximal end of the venous cannula (b) is attached so as to send blood to the external oxygenation device and the proximal end of the arterial cannula (a) is attached so as to receive blood from the oxygenation device, wherein the dual lumen portion (ii) of the catheter enters the vena cava and the end of the arterial cannula (a) is inserted into the left atrium and the end of the venous cannula (b) in the central segment (ii) is inserted into the vena cava.

Figure 3A:
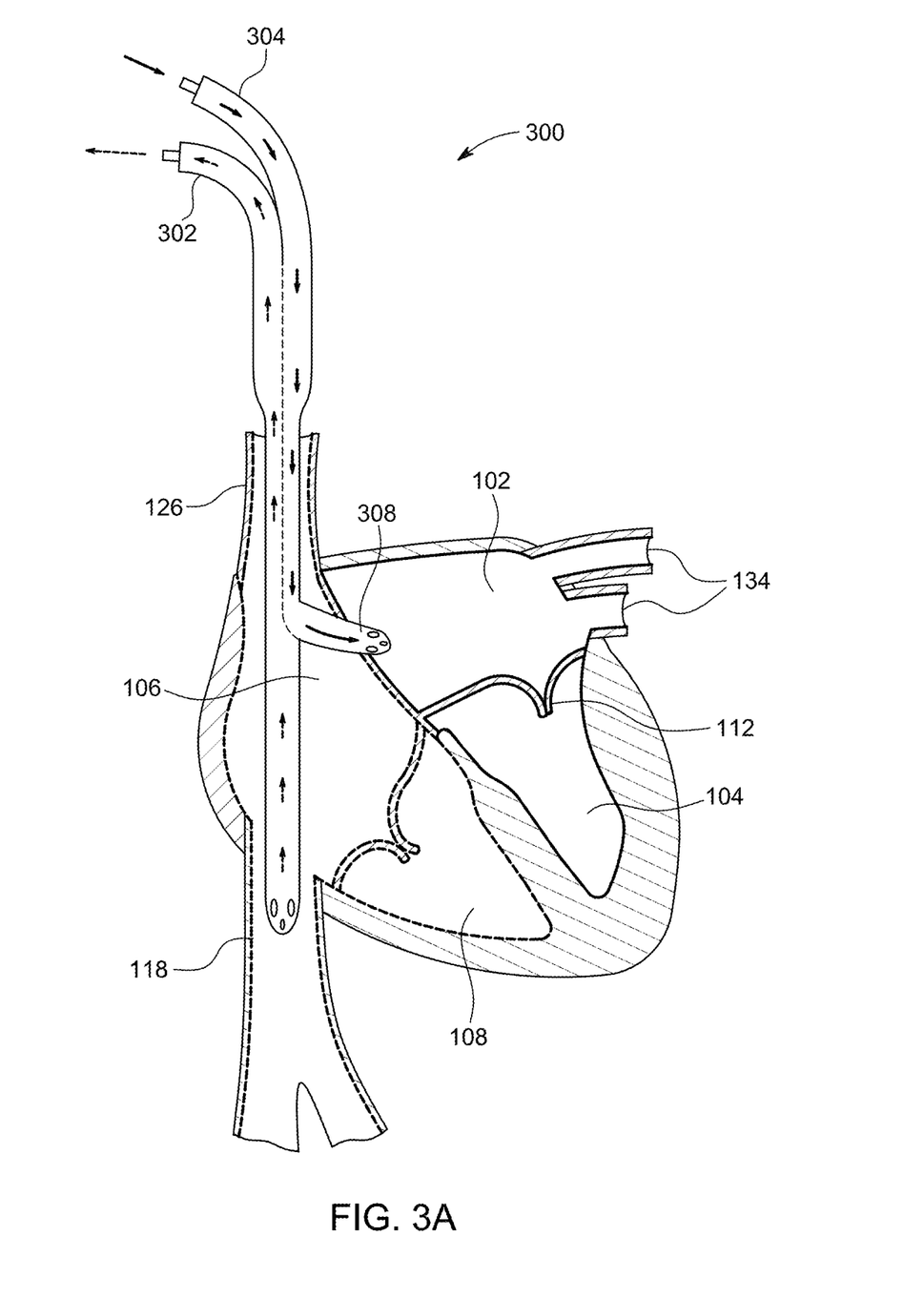
FIG. 3A illustrates an embodiment of the invention depicting single downward entry point for a dual lumen catheter 300 via the superior vena cava. Oxygenated blood enters via arterial catheter 304 which enters the RA 106 via the SVC 126 and branches 308 through the atrial septum into the left atrium 102. Venous catheter 302 enters the SVC and RA and receives blood from the IVC 118. Also depicted are the right ventricle 108, left ventricle 104, mitral valve 112 and pulmonary veins 134.

In this embodiment, the single entry point may be the superior vena cava as shown by FIG. 3A and cannula (b) positioned in the inferior vena cava. In such an ECMO circuit, venous blood low in oxygen is received by venous cannula (b) 302 from the inferior vena cava, transported or pumped into the external oxygenation device to produce oxygenated blood, and then the oxygenated blood is infused into the left atrium via arterial cannula (a) 304, which functions as a holding chamber for the oxygenated blood and acts as a pump to send the oxygenated blood to the left ventricle and then to the rest of the body. FIG. 3A shows a branch 308 to arterial cannula 304 through one or more holes in the atrial septum through which blood can be infused into the left atrium 102. This branch of the cannula carrying oxygenated blood pumps the blood into the left atrium through an opening that is typically made under imaging guidance (ECHO/Cath). The cannula receiving venous blood may receive it through openings at its proximal (top) positioned in the superior vena cava and/or distal (bottom) end which is inserted into the inferior vena cava. Alternatively to insertion via the superior vena cava, the device may be used from the groin through the femoral vein and inserted through the inferior vena cava, see FIG. 3B. In this arrangement, the catheter does not usually obstruct the whole of the lumen of the SVC and blood still drains to the RA as veins are expansile structures. There is also a right SVC. Similarly, the IVC is quite large and a catheter usually does not obstruct the whole of the lumen for similar reasons.

Figure 3B:
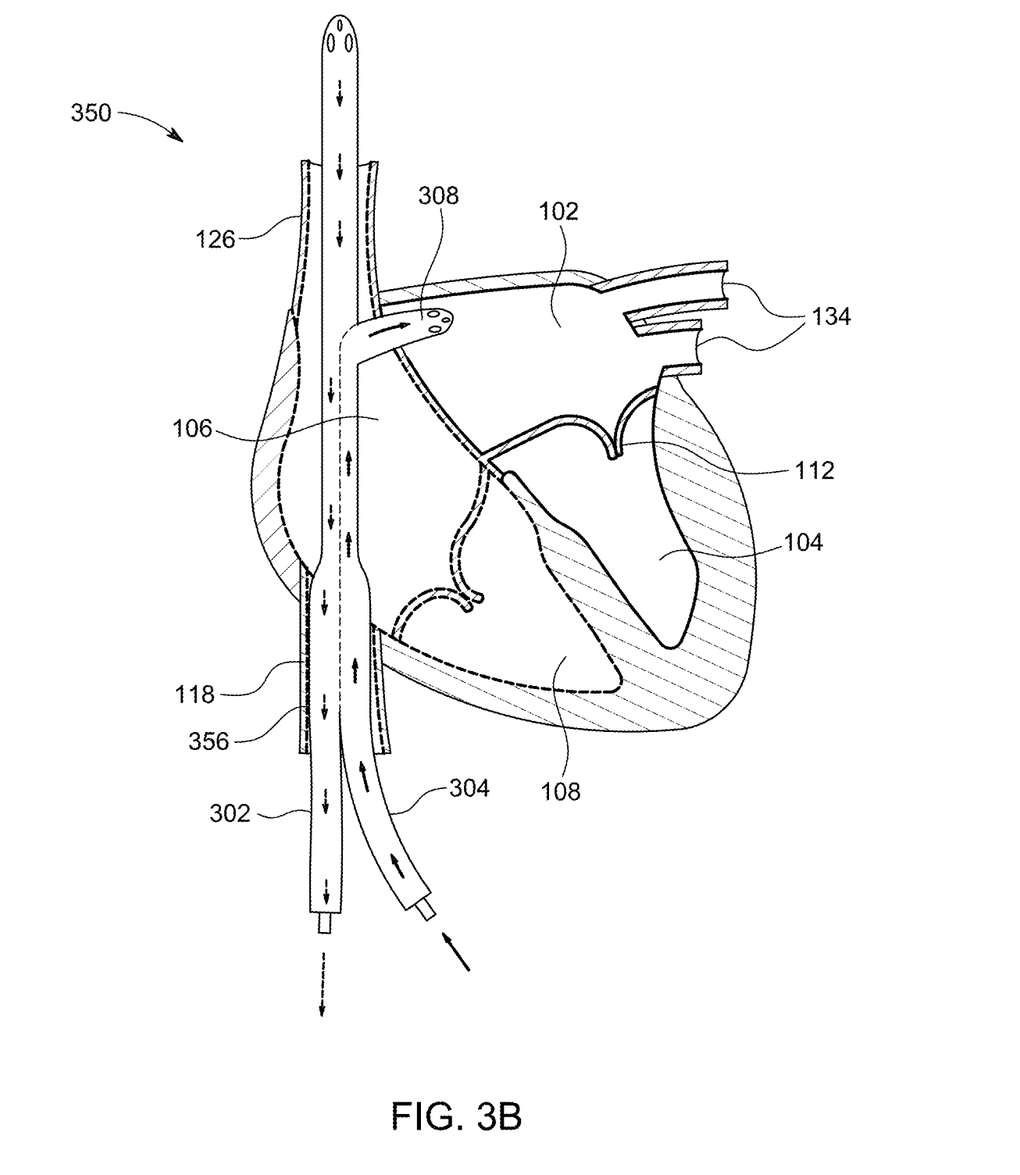
FIG. 3B illustrates an embodiment of the invention depicting single upward entry point for dual lumen catheter 350 via the inferior vena cava 118. Oxygenated blood enters via arterial catheter 304 which enters the RA 106 via the IVC 118 and branches 308 through the atrial septum into the left atrium 102. Venous catheter 302 enters the RA via the IVC and receives blood from the SVC 126. Also depicted are the right ventricle 108, left ventricle 104, mitral valve 112 and pulmonary veins 134.
Figure 3C:
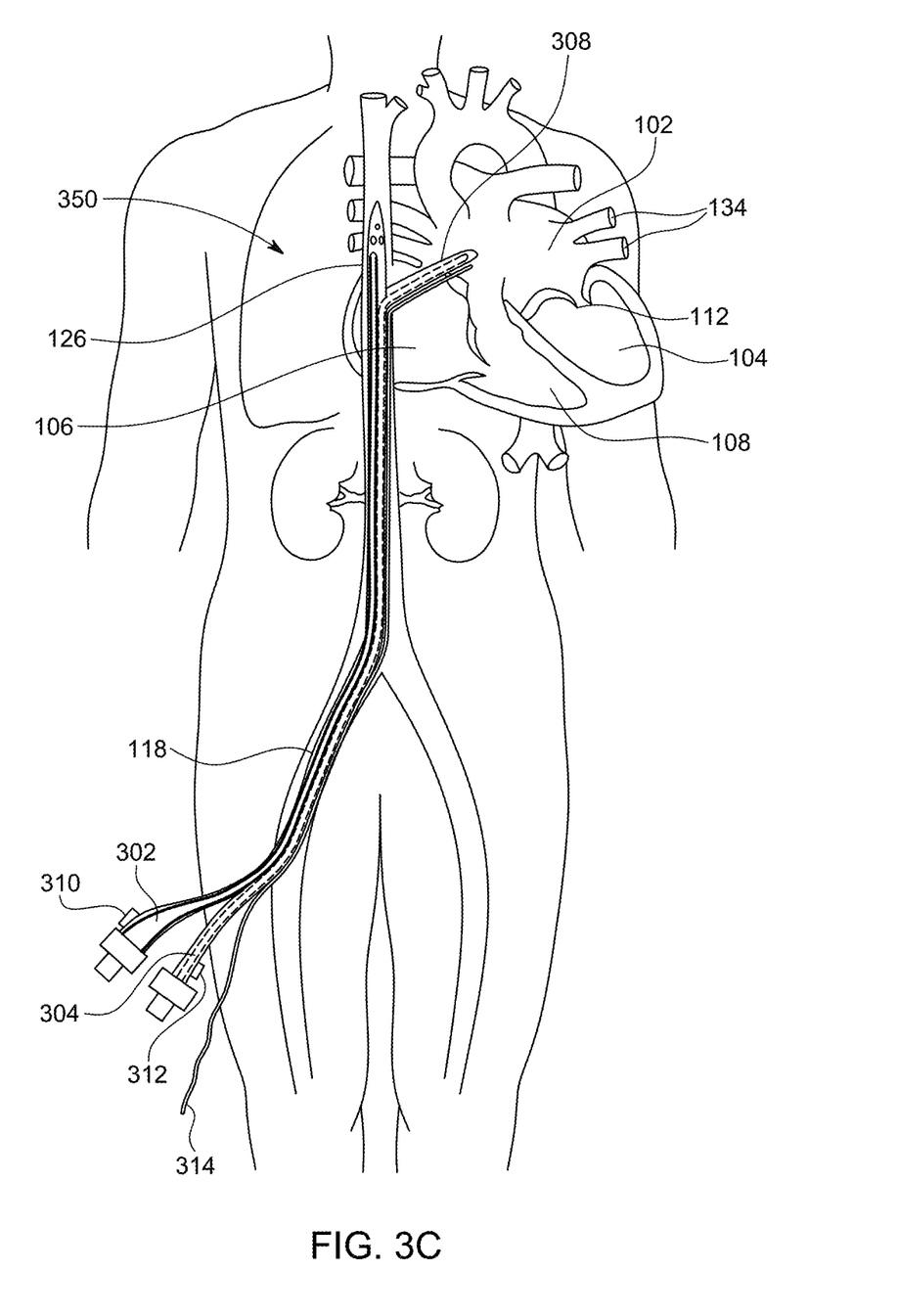
FIG. 3C provides an expanded illustration depicting single upward entry point for dual lumen catheter 350 via a femoral or groin vein and the inferior vena cava 118. Arterial extension port 304 is color coded by tag 314 and venous port 302 is color coded by tag 310. Embedded very thin guidewire 314 to steer catheter 304 to LA under ECHO guidance. The branch of arterial catheter 304 into the LA is shown as 308.
Figure 4A:
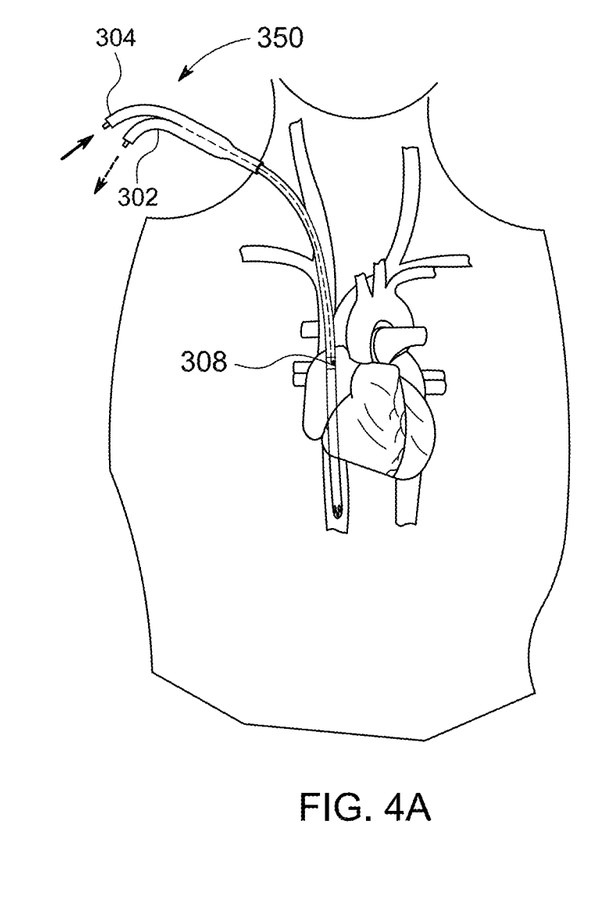
FIG. 4A. Placement detail for single point insertion of the dual lumen catheter via the SVC showing position of arterial catheter 304 and branch 308 of arterial catheter inserted into LA; and venous catheter 302 as inserted into the IVC.
Figure 4B:
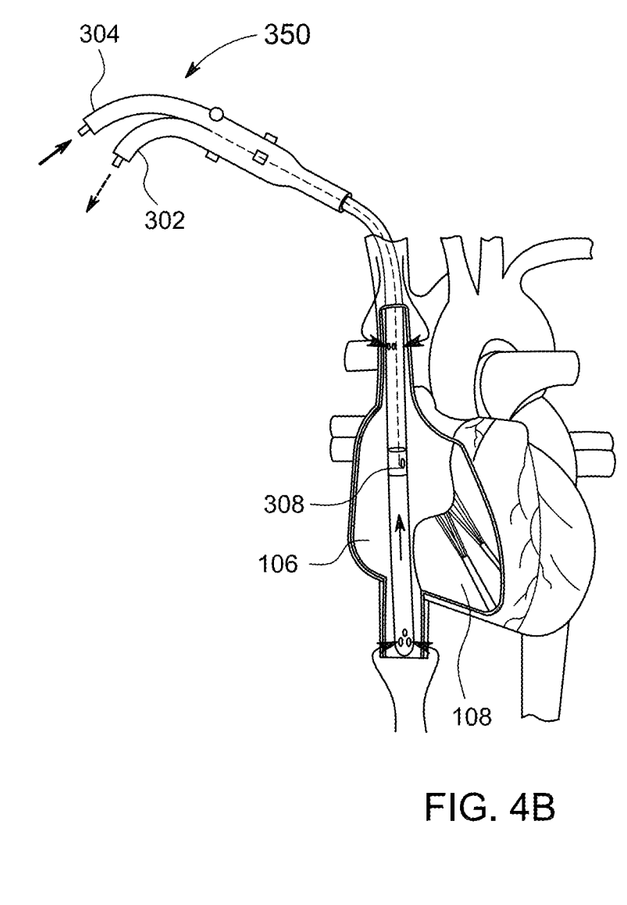
FIG. 4B. Placement detail for single point insertion of the dual lumen catheter via the SVC showing position of arterial catheter 304 and branch 308 of arterial catheter inserted into LA; and venous catheter 302 as inserted into the IVC. Right ventricle is indicated by 108.

Alternatively, the single entry point may be the inferior vena cava and cannula (b) 302 is positioned to receive venous blood from the superior vena cava as shown by FIG. 3B. In such an ECMO circuit, venous blood low in oxygen is received by cannula (b) 302 from the superior vena cava, transported or pumped into the external oxygenation device to produce oxygenated blood, and then the oxygenated blood is infused via cannula (a) into the left atrium, which functions as a holding chamber for the oxygenated blood and acts as a pump to send the oxygenated blood to the left ventricle and then to the rest of the body.

This method may be used to treat a patient in need of ECMO including a patient with right heart failure or partial right heart failure, such as a patient having damage caused by viral, bacterial, fungal, or parasite infection. Some patients, particularly neonates, may have a congenital right heart defect. In other embodiments of this method the patient will have respiratory failure or insufficiency.

In this method the dual lumen catheter is inserted via the superior vena cava (IVC) leaving the inferior vena cava unobstructed by the catheter or the dual lumen catheter is inserted via the inferior vena cava (IVC) leaving the superior vena cava unobstructed by the catheter.

ECMO Conditions.

Criteria for the initiation of ECMO vary by institution, but generally include acute severe cardiac or pulmonary failure that is potentially reversible and unresponsive to conventional management. Examples of clinical situations that may prompt the initiation of ECMO include the following: hypoxemic respiratory failure with a ratio of arterial oxygen tension to fraction of inspired oxygen ($PaO_2/FiO_2$) of <100 mmHg despite optimization of the ventilator settings, including the fraction of inspired oxygen ($FiO_2$), positive end-expiratory pressure (PEEP), and inspiratory to expiratory (I:E) ratio; hypercapnic respiratory failure with an arterial pH<7.20; refractory cardiogenic shock; cardiac arrest; failure to wean from cardiopulmonary bypass after cardiac surgery; as a bridge to either heart transplantation or placement of a ventricular assist device; as a bridge to lung transplantation; septic shock is a more controversial but increasingly studied use of ECMO; hypothermia, with a core temperature between 28 and 24° C. and cardiac instability, or with a core temperature below 24° C. In those with cardiac arrest or cardiogenic shock, ECMO appears to improve survival and good outcomes.

Right Side Heart Failure.

ECMO may be used to treat particular types of right-sided heart failure. Right-sided heart failure is often caused by pulmonary heart disease (cor pulmonale), which is typically caused by difficulties of the pulmonary circulation, such as pulmonary hypertension or pulmonic stenosis. Physical examination may reveal pitting peripheral edema, ascites, liver enlargement, and spleen enlargement. Jugular venous pressure is frequently assessed as a marker of fluid status, which can be accentuated by eliciting hepatojugular reflux. If the right ventricular pressure is increased, a parasternal heave may be present, signifying the compensatory increase in contraction strength. Backward failure of the right ventricle leads to congestion of systemic capillaries. This generates excess fluid accumulation in the body. This causes swelling under the skin (termed peripheral edema or anasarca) and usually affects the dependent parts of the body first (causing foot and ankle swelling in people who are standing up, and sacral edema in people who are predominantly lying down). Nocturia (frequent nighttime urination) may occur when fluid from the legs is returned to the bloodstream while lying down at night. In progressively severe cases, ascites (fluid accumulation in the abdominal cavity causing swelling) and liver enlargement may develop. Significant liver congestion may result in impaired liver function (congestive hepatopathy), and jaundice and even coagulopathy (problems of decreased or increased blood clotting) may occur.

Respiratory Failure.

ECMO may be used to treat particular kinds of respiratory failure. Respiratory failure results from inadequate gas exchange by the respiratory system, meaning that the arterial oxygen, carbon dioxide or both cannot be kept at normal levels. A drop in the oxygen carried in blood is known as hypoxemia; a rise in arterial carbon dioxide levels is called hypercapnia. Respiratory failure is classified as either Type 1 or Type 2, based on whether there is a high carbon dioxide level. The definition of respiratory failure in clinical trials usually includes increased respiratory rate, abnormal blood gases (hypoxemia, hypercapnia, or both), and evidence of increased work of breathing. Respiratory failure causes an altered mental status due to ischemia in the brain.

Patients.

The single entry point dual lumen catheter as disclosed herein may be used for subjects in need of ECMO, including those having right heart failure, partial right heart failure, lung failure or insufficiency. Patients include neonates, babies, children and adults, for example, a patient may be male or female and 0, <0.5, 0.5, 1, 2, 5, 10, 20, 30, 40, 50, 60, 70, 80, 90, 100 or >100 years of age. A neonate/baby patient may have persistent pulmonary hypertension, meconium aspiration syndrome, sepsis or infection, pneumonia, congenital diaphragmatic hernia, congenital heart disease, post-op lung shock, or hyaline membrane disease. An older child may require post-op cardiac repair, have myocarditis, sepsis, pneumonia, aspiration pneumonia, have asthma, have nearly drowned, or ingested hydrocarbons such as lighter fluid or turpentine. An adult patient may have underlying disease which has a reasonable likelihood of reversal, septic shock, pneumonia, or pulmonary failure.

Ecmo Surgery.

Being placed on ECMO requires a surgical procedure which is usually done in a patient's room. The patient is sedated and given pain medication and an anti-coagulant to minimize blood clotting. A surgeon, assisted by an operating room team, inserts the ECMO catheters into the insertion point, here, into the superior or inferior vena cava. Once inserted through the vena cava, the arterial branch of the catheter is inserted into the left atrium. An x-ray is then taken to ensure the arterial and venous tubes are in the right places. Usually a patient on the ECMO pump will also be on a ventilator which helps the lungs to heal. While on ECMO, the patient will be monitored by specially trained nurses and respiratory therapists, as well as by the surgeon and surgical team. Since the patient is typically sedated and fitted with a breathing tube, supplemental nutrition will be provided either intravenously or through a nasal-gastric tube.

While on ECMO, the patient may be given certain medications including: heparin to prevent blood clots; antibiotics to prevent infections; sedatives to minimize movement and improve sleep; diuretics to help the kidney get rid of fluids; electrolytes to maintain the proper balance of salts and sugars; and blood products to replace blood loss. Discontinuing ECMO requires a surgical procedure to remove the tubes. Multiple tests are usually done prior to the discontinuation of ECMO therapy to confirm that the heart and lungs are ready. Once the ECMO cannulas are removed, the vessels will need to be repaired. This can be done either at the bedside or in the operating room. The doctor will use small stitches to close the spot where the tubes were placed. The patient will be asleep and monitored for this process. Even though the patient is off the ECMO, the patient may still need to be on a ventilator.

In one embodiment, after cleaning the groin area (for femoral vein access) or neck (for internal jugular vein access), a needle is inserted and once the proper position is confirmed a guide wire is passed into the IVC up to the RA part of the heart as confirmed by echocardiogram (Echo).

The incision is then enlarged to accommodate catheter entry and a dilator is passed to increase the entry into the lumen. The tip of the catheter is passed over the guide wire until it reaches the SVC (from the groin/femoral approach) or the IVC (from the neck approach).

The position of the left atrial extension is placed on the atrial septum, which is confirmed by color coding of the insertion points and by Echo.

A guide wire, which is hard, sharp and has a cutting tip, is passed through the arterial port and the atrial septum is punctured under Echo guidance and the hole is enlarged with a balloon which is the same size of the LA catheter to avoid leakage of blood from the LA to the RA. Under Echo guidance, the left atrial extension is separated and guided into the left atrium, for example, using a guidewire embedded in the cannula. The separation is performed by pulling on the wire that attaches on the surface of the arterial extension. Once the position is confirmed in the LA by Echo, then ECMO circuit is initiated. A chest X-ray is done to confirm the position using radio-opaque markers.

Imaging. An ECMO procedure is typically performed in conjunction with medical imaging such as with fluoroscopy and/or transesophageal echocardiogram (TEE). Other modes of medical imaging may be selected by those skilled in the endosurgical arts such as from those described by hypertext transfer protocol secure://en.wikipedia.org/wiki/Cardiac_imaging (incorporated by reference, last accessed Sep. 17, 2019) such as by ultrasound, magnetic resonance imaging (MM), computed tomography (CT), or nuclear medicine imaging with PET or SPECT. These cardiac techniques are otherwise referred to as echocardiography, cardiac MM, cardiac CT, cardiac PET and cardiac SPECT myocardial perfusion imaging.

ECMO Cannula (Component of Catheter).

Those skilled in the medical arts may select a cannula size based on weight of the patient, for example, as ranging from <10, 10, 11, 12, 13, 14, 15, 16, 17, 18, 19, 20, 21, 22, 23, 24, 25, 26, 27, 28, 29, 30, 31, or >31 French (Fr), or as shown by the following table. An ECMO cannula is sometimes referred to as a catheter or as tubing.

| Single Lumen Cannulation (VA or VA) | | |
| --- | --- | --- |
| Patient Size (kg) | Drainage cannula (Fr) | Patient return cannula (Fr) |
| 2 | 10 | 10 |
| 3-6 | 12/14 | 10 |
| 6-8 | 14 | 12 |
| 8-14 | 17 | 14 |
| 15-20 | 17 | 14 |

-continued

Single Lumen Cannulation (VA or VA)

| Patient Size (kg) | Drainage cannula (Fr) | Patient return cannula (Fr) |
|---|---|---|
| 20-30 | 17 | 17 |
| 30-40 | 21 | 17 |
| >40 | 28 | 21 |

Typically the sizes of the cannulas vary depending upon the body surface area of a patient. They may range from about 13 Fr. (4.3 mm) up to 31 Fr (10.3 mm) in diameter, have an insertable length of about 11 to 31 cm. The left atrial extension may range in length from about 2 to 4 cm. The catheter going into the left atrium may be half-circle or C-shaped in cross-section. When joined arterial and venous catheters transit the insertion point in the vena cava, their cross-sections may be circular.

The catheter may comprise or consist of a range of polymers including silicone rubber, nylon, polyurethane, polyethylene terephthalate (PET), latex, and thermoplastic elastomers. Silicone is one of the most common choices because it is inert and unreactive to body fluids and a range of medical fluids with which it might come into contact. A catheter may be reinforced. Suitable catheters are commercially available. Preferred catheter materials include kink-resistant material or wire-reinforced material, radio-opaque material and/or heparin-coated material. Catheters may contain a deflectable inner membrane, distal & proximal drainage ports, and have separate drainage and infusion ports.

Ecmo Machine.

The ECMO machine, often referred to as a "circuit," is large and contains sterile plastic tubing that moves blood from the patient to the "ECMO lung" or external oxygenation device and then back to the patient. The ECMO lung adds oxygen to the blood and removes carbon dioxide, as a healthy lung would.

An ECMO machine (oxygenator) comprises an oxygenating chamber in which gas exchange between a gas flow providing a supply of fresh gas and the blood of a patient takes place. Blood from the body of the patient is pumped through a fluid line, such as cannula (b), to the oxygenator, enters the oxygenating chamber through a blood inlet, passes through the oxygenating chamber, leaves the oxygenating chamber again through a blood outlet and is returned from the oxygenator to the patient. Moreover, a gas flow of fresh gas enters the oxygenating chamber through a gas inlet, is passed through the oxygenating chamber and leaves the oxygenating chamber again through a gas outlet. In the oxygenating chamber, oxygen (and, if present in the gas flow, other gases such as inhalational anesthetics) are transferred from the gas flow into the blood, while other gases, such as carbon dioxide, are transferred from the blood into the gas flow.

ECMO systems are commercially available, for example, from Medico engineering, hypertext transfer protocol:// www.medico-eng.com/en/products.php?id=51 incorporated by reference, last accessed Sep. 17, 2019) and from the manufactures listed by the Extracorporeal Life Support Organization (hypertext transfer protocol secure:://www.elso.org/Default.aspx?TabID=129 (incorporated by reference, last accessed Sep. 17, 2019). ECMO components can include a blood warming device, heat exchanger, membrane oxygenator (gas exchange device), roller or centrifugal pump, circuit tubing and catheters specific to the site of access, for example, to the superior vena cava or inferior vena cava, or to the left atrium. Other components include blood flow and pressure monitors, continuous oxyhemoglobin satural monitors, circuit access sites, or a bridge connecting the delivery (venous access cannula) and infusion branches of the limbs of the circuit connecting to the exterior oxygenation device.

Other components of an ECMO device or system and surgical use thereof include those described by and incorporated by reference to hypertext transfer protocol secure:// en.wikipedia.org/wiki/Extracorporeal_membrane_oxygenation (last access Oct. 8, 2019).

ECMO cannulae are commercially available and may be modified or designed by those skilled in the medical arts to conform to the designs required by the invention. Venous cannulas may range in size from 23-29 French steel wire reinforced. Arterial cannulas may range in size from 19 to 21 French steel wire reinforced. A cannula may vary in insertion length from about 15 to 55 cm. The size of a venous cannula directly determine blood flow and the largest possible venous cannula preferably is used to maximize flow and achieve a target output such as a VV ECMO flow of about 40, 50, 60 to 70 cc/kg/min. Some representative cannulas, supplies and surgical procedures are described by an incorporated by reference to hypertext transfer protocol:// edecmo.org/logistics/vv-ecmo/(last accessed Oct. 8, 2019).

The tubing forming lumens (a) and (b) is typically a plastic tubing, such as silicone tubing, polyvinyl chloride, or tissue-friendly polyurethane, suitable for transporting blood. The tubing or fluid lines is made from a material that is inert with respect to blood, impermeable to blood and substantially impermeable to gases dissolved in blood, such as tubing made from a suitable polymeric material.

Connective tubing between the oxygenator and the cannulae is preferably as short and narrow as feasible in order to reduce blood volume outside the subject. However, the potential movements of the subject should be considered in the length of the tubing. In a particular embodiment, the tubing is about 12 inches or less from the cannula to the oxygenator. In a particular embodiment, the tubing is lined with anti-clotting compounds or materials (e.g., immobilized polypeptide and/or heparin) (i.e., the tubing is clot resistant). The external portion of the cannulas may be fitted with a sleeve (e.g., to permit increased tension of the stabilizing sutures). The sleeve may be made of silicone and may be, for example, about 1-10 cm in length, particularly about 3-5 cm in length. In some embodiments, the cannulae may be sutured in place.

Human Heart Anatomy.

The human heart has four chambers: two upper chambers called atria and two lower ones called ventricles. The right atrium and right ventricle together make up the "right heart," and the left atrium and left ventricle make up the "left heart." A wall of muscle called the septum separates the two sides of the heart. See FIG. 1.

The weight and dimensions of the human heart and its components range in size depending on factors like age, sex and other physical features. The size and weight of the heart and its chambers and membranes may be determined or estimated by methods known in the art including by medical imaging such as echocardiography. Some typical ranges and values are described below.

The left ventricular end-diastolic dimension ranges from about 36-56 mm, typically about 48 mm.

The right ventricular end-diastolic dimension ranges from about 10 to 26 mm.

The left ventricular end-systolic dimension ranges from about 20 to 40 mm and the right ventricular end systolic dimension ranges from about 10 to 26 mm.

The interventricular septal end diastolic dimension (thickness of the interventricular septum) ranges from 7 to 11 mm, typically about 8.3 mm.

The left ventricular end diastolic posterior wall dimension ranges from 7 to 11 mm, typically about 8.3 mm.

The mean left ventricular myocardial thickness in women ranges from about 4 to 8 mm and in men ranges from about 5 to 9 mm.

The mean right ventricular myocardial thickness ranges from about 4 to 7 mm.

The left ventricular end systolic dimension is about 16 mm.

The left atrial dimension ranges from about 24 to 40 mm.

The normal right atrial length (long axis) ranges from about 29-45 mm but may be enlarged up to about 55 mm by disease.

The superior vena cava is a large diameter in a normal adult about 13-30 mm, typically above 20 mm) short length vein that receives venous return from the upper half of the body.

The inferior vena cava has a diameter of about 15-17 mm that receives venous return from the lower half of the body.

Those skilled in the medical and surgical arts can select or tailor the cannula components of the device of the invention to be of an appropriate size to deliver blood from the superior and/or inferior vena cava to an ECMO outside of the body and to infuse oxygenated blood from the ECMO into the right atrium as depicted in the figures.

Terminology

Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When an element is referred to as being "over," "on," "attached" to, "connected" to, "coupled" with, "contacting," "in fluid communication with," etc., another element, it can be directly over, on, attached to, connected to, coupled with, contacting, or in fluid communication with the other element or intervening elements may also be present. In contrast, when an element is referred to as being "directly over," "directly on," "directly attached" to, "directly connected" to, "directly coupled" with, "directly contacting," or in "direct fluid communication" with another element, there are no intervening elements present. It will also be appreciated that references to an element that is disposed "adjacent" another element may have portions that overlap or underlie the adjacent element. The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A dual lumen single entry point catheter, comprising:
   (i) a proximal segment comprising a section of two unjoined cannulas one suitable for transporting oxygenated blood, cannula (a), and the other suitable for transporting venous blood, cannula (b),
   (ii) a central segment wherein cannula (a) and cannula (b) are longitudinally joined, and
   (iii) a distal segment wherein cannula (a) and cannula (b) are not longitudinally joined;
   wherein cannulas (a) and (b) in the proximal segment (i) are configured to operably connect to an exterior oxygenation device with cannula (a) connected so as to receive oxygenated blood from the exterior oxygenation device and cannula (b) connected so as to deliver venous blood to the exterior oxygenation device,
   wherein in the central segment (ii) the longitudinally joined cannula (a) and cannula (b) are configured to make a single point insertion into the right atrium of a heart via the vena cava,
   wherein in distal segment (iii) cannula (a) is configured so as to penetrate an interatrial septum between the right and left atrium and enter the left atrium so as to be able to deliver oxygenated blood into the left atrium,
   wherein in distal segment (iii) cannula (b) is configured to position straight in the right atrium and enter the vena cava so as to receive venous blood from the vena cava and right atrium through openings at a terminal bottom end and deliver it to the exterior oxygenation device, and
   wherein in distal section (iii) cannula (a) is about 2-3 cm long and cannula (b) is about 6-8 cm long.

2. The dual lumen single entry port catheter of claim 1, which is configured so as to permit a single point insertion to occur via the superior vena cava (SVC) and wherein the cannula (b) is configured to receive venous blood from the inferior vena cava.

3. The dual lumen single entry port catheter of claim 1, which is configured so as to permit a single point insertion to occur via the inferior vena cava (IVC) and wherein the cannula (b) is configured to receive venous blood from the superior vena cava.

4. The dual lumen single entry port catheter of claim 1, wherein cannula (a) and cannula (b) have a gauge ranging from 10 to 20 French (Fr).

5. The dual lumen single entry port catheter of claim 1, wherein cannula (a) and cannula (b) have a gauge ranging from >20 to 30 French.

6. The dual lumen single entry port catheter of claim 1, wherein cannula (a) and cannula (b) have a gauge of >30 French.

7. The dual lumen single entry port catheter of claim 1, further comprising:
   a guide wire,
   wherein the guide wire is configured to guide the distal segment (iii) of cannula (a) to penetrate the interatrial septum between the right and left atrium and enter the left atrium.

8. The dual lumen single entry port catheter of claim 1, wherein the cannula (a) and the cannula (b) are color coded to indicate ports of drainage and infusion and position in the heart.

9. A method for treating a patient having right heart failure, lung failure, or both, comprising:
   positioning a dual lumen single entry point catheter into a heart of the patient; and
   connecting an exterior oxygenation device to the dual lumen single entry point catheter,
   wherein the dual lumen single entry point catheter comprises:
   (i) a proximal segment comprising a section of two unjoined cannulas one suitable for transporting oxygenated blood, cannula (a), and the other suitable for transporting venous blood, cannula (b),
   (ii) a central segment wherein cannula (a) and cannula (b) are longitudinally joined, and
   (iii) a distal segment wherein cannula (a) and cannula (b) are not longitudinally joined;
   wherein cannulas (a) and (b) in the proximal segment (i) are operably connected to the exterior oxygenation device with cannula (a) connected so as to receive oxygenated blood from the exterior oxygenation device and cannula (b) connected so as to deliver venous blood to the exterior oxygenation device, wherein in the central segment (ii) the longitudinally joined cannula (a) and cannula (b) make a single point insertion into the right atrium of a heart via the vena cava, wherein in distal segment (iii) cannula (a) penetrates an interatrial septum between the right and left atrium and enters the left atrium so as to be able to deliver oxygenated blood into the left atrium, wherein in distal segment (iii) cannula (b) is positioned straight in the right atrium and enters the vena cava so as to receive venous blood from the vena cava and the right atrium through openings at a terminal bottom end and deliver it to the exterior oxygenation device, and wherein in distal section (iii) cannula (a) is about 2-3 cm long and cannula (b) is about 6-8 cm long.

10. The method of claim 9, further comprising:

pulling a guide wire of the dual lumen single entry point catheter to guide the distal segment (iii) of cannula (a) to penetrate the interatrial septum between the right and left atrium and enter the left atrium.

11. The method of claim 9, wherein the dual lumen single entry point catheter is positioned into the heart of the patient via a single downward entry point.

12. The method of claim 9, wherein the dual lumen single entry point catheter is inserted via the superior vena cava (SVC) and wherein the cannula (b) is configured to receive venous blood from the inferior vena cava.

13. The method of claim 9, wherein the dual lumen single entry point catheter is inserted via the inferior vena cava (IVC) and wherein the cannula (b) is configured to receive venous blood from the superior vena cava.

14. The method of claim 9, wherein cannula (a) and cannula (b) have a gauge ranging from 10 to 20 French (Fr).

15. The method of claim 9, wherein cannula (a) and cannula (b) have a gauge ranging from >20 to 30 French.

16. The method of claim 9, wherein cannula (a) and cannula (b) have a gauge of >30 French.

* * * * *